US012138101B2

(12) United States Patent
Han et al.

(10) Patent No.: US 12,138,101 B2
(45) Date of Patent: Nov. 12, 2024

(54) X-RAY IMAGING APPARATUS

(71) Applicants: VATECH Co., Ltd., Gyeonggi-do (KR); VATECH EWOO Holdings Co., Ltd., Gyeonggi-do (KR)

(72) Inventors: Tae Hee Han, Gyeonggi-do (KR); Yong Joo Yang, Gyeonggi-do (KR); Sung Hwan Lim, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 0 days.

(21) Appl. No.: 17/462,290

(22) Filed: Aug. 31, 2021

(65) Prior Publication Data

US 2022/0061792 A1    Mar. 3, 2022

(30) Foreign Application Priority Data

Aug. 31, 2020   (KR) .................. 10-2020-0110099
Aug. 25, 2021   (KR) .................. 10-2021-0112374

(51) Int. Cl.
*A61B 6/00*     (2024.01)
*A61B 6/04*     (2006.01)
*A61B 6/46*     (2024.01)

(52) U.S. Cl.
CPC ............ *A61B 6/544* (2013.01); *A61B 6/0407* (2013.01); *A61B 6/4435* (2013.01);
(Continued)

(58) Field of Classification Search
CPC ..... A61B 6/032; A61B 6/0407; A61B 6/4435; A61B 6/4476; A61B 6/466; A61B 6/467; A61B 6/488; A61B 6/544; A61B 6/545
See application file for complete search history.

(56) References Cited

U.S. PATENT DOCUMENTS

2003/0016778 A1*  1/2003  Tachizaki ............... G16H 40/63
                                                      378/4
2006/0269113 A1*  11/2006  Gundel ................. G06T 11/006
                                                      382/131

(Continued)

FOREIGN PATENT DOCUMENTS

EP          3597106 A1      1/2020

OTHER PUBLICATIONS

European Patent Office, European Search Report of corresponding EP Patent Application No. 21193982.2, Jan. 31, 2022.

*Primary Examiner* — Dani Fox
*Assistant Examiner* — Soorena Kefayati
(74) *Attorney, Agent, or Firm* — IP Legal Services, LLC

(57) ABSTRACT

Provided is an X-ray image apparatus. The X-ray imaging apparatus include an imaging body and a control circuit. The image body acquires X-ray image data of an object and includes an X-ray generation device and an X-ray sensing device. The X-ray generating device and the X-ray sensing device are disposed to face each other with the object in between. The control circuit reconfigures an X-ray image of the object based on the X-ray image data, acquire size information of the object, rotate the X-ray generation device and the X-ray sensing device about a rotation axis between the X-ray generation device and the X-ray sensing device, and move the object along a direction of the rotation axis with respect to the X-ray generation device and the X-ray sensing device when acquiring the X-ray image data.

7 Claims, 7 Drawing Sheets

(52) U.S. Cl.
CPC ............ *A61B 6/4476* (2013.01); *A61B 6/466* (2013.01); *A61B 6/467* (2013.01)

(56) References Cited

U.S. PATENT DOCUMENTS

| | | | |
|---|---|---|---|
| 2012/0243655 A1* | 9/2012 | Ninomiya | A61B 6/4035 378/8 |
| 2014/0270053 A1* | 9/2014 | Larson | A61B 6/5258 378/4 |
| 2016/0019701 A1* | 1/2016 | Visser | A61B 5/0059 378/19 |
| 2016/0220215 A1* | 8/2016 | Kwak | A61B 6/10 |
| 2016/0242727 A1* | 8/2016 | Flohr | A61B 6/032 |
| 2016/0262714 A1* | 9/2016 | Krauss | A61B 6/544 |
| 2016/0296196 A1* | 10/2016 | Boedeker | A61B 6/032 |
| 2018/0049714 A1* | 2/2018 | Nett | A61B 6/542 |
| 2021/0251584 A1* | 8/2021 | Nae | A61B 6/032 |

* cited by examiner

X-RAY IMAGING APPARATUS

CROSS REFERENCE TO RELATED APPLICATION

The present application claims priority to Korean Patent Application Nos. 10-2020-0110099 and 10-2021-0112374, respectively field on Aug. 31, 2020 and Aug. 25, 2021, the entire contents of which is incorporated herein for all purposes by this reference.

BACKGROUND OF THE INVENTION

Field of the Invention

The present disclosure relates to an X-ray imaging apparatus and, more particularly, to an X-ray imaging apparatus capturing and displaying an X-ray image of an object.

Description of the Related Art

Among X-ray imaging apparatuses in the medical field, a computer tomography (CT) apparatus is an apparatus that transmits X-rays through an object at various angles, obtains X-ray image data that is X-ray transmission data in various directions on the object, reconfigures the X-ray image data, and thus displays an internal structure of the object as a three-dimensional X-ray image.

FIG. 1 is a cross-sectional view illustrating a CT apparatus in the related art;

As illustrated in FIG. 1, the CT apparatus may include an X-ray generation module 11, an X-ray sensing module 12, and a housing 13.

The X-ray generation module 11 generates X-rays 14, and transmits the X-rays 14 through an object 15. The X-ray sensing module 12 detects the X-rays 14 passing through the object 15 and generates X-ray image data that is an electric signal in accordance with an X-ray dose on a per-position basis.

The housing 13 is provided in the form of a doughnut. The object 15 is accommodated into an opening portion in the center of the housing 13. The X-ray generation module 11 and the X-ray sensing module 12 are mounted within the housing 13.

The X-ray generation module 11 and the X-ray sensing module 12 face each other within the housing 13 with the object 15 in between. The X-ray generation module 11 and the X-ray sensing module 12, while rotating around the object 15 about a rotation axis therebetween, emits and detects the X-rays 14 and thus acquires pieces of X-ray image data in various directions on the object 15.

The pieces of X-ray image data in various directions that are obtained in this manner are reconfigured in a control apparatus, such as a computer, and are realized as a CT image that is a three-dimensional image of the object 15.

In a general-type CT apparatus, the object 15 lies on a bed or an inspection table having a shape similar to that of the bed. Along with the object 15, the inspection table passes through the opening portion in the housing 13 and is moved in a straight line along a direction of the rotation axis between the X-ray generation module 11 and the X-ray sensing module 12. In this manner, through spiral- or helical-type X-ray imaging that is performed while rotating the X-ray generation module 11 and the X-ray sensing module 12 and moving the object 15 in a straight line, the pieces of X-ray image data in various directions on the object 15 may be obtained successively along a length direction of the object 15. For reference, a distance by which the inspection table is moved each time the X-ray generation module 11 and the X-ray sensing module 12 are rotated is defined as a pitch.

The CT apparatus in the related art acquires the X-ray image data by rotating fan beam X-rays at a high speed with a small pitch being maintained. Thus, the imaging time is increased. Furthermore, in a case where the object 15 has a small size, an amount of radiation exposure is unnecessarily increased.

The foregoing is intended merely to aid in the understanding of the background of the present disclosure, and is not intended to mean that the present disclosure falls within the purview of the related art that is already known to those skilled in the art.

SUMMARY OF THE INVENTION

An objective of the present disclosure is to provide an X-ray imaging apparatus having an X-ray imaging mechanism optimized according to a size of an object and thus capable of decreasing the imaging time and an amount of radiation exposure.

According to an aspect of the present disclosure, there is provided an X-ray imaging apparatus including: an imaging body configured to include an X-ray generation module and an X-ray sensing module that face each other with an object in between and acquire X-ray image data; an image formation module configured to reconfigure an X-ray image of the object on the basis of the X-ray image data; a size information acquisition module configured to acquire size information on the object using the X-ray image; and a control module configured to rotate the X-ray generation module and the X-ray sensing module about a rotation axis between the X-ray generation module and the X-ray sensing module and relatively move the object along a direction of the rotation axis with respect to the X-ray generation module and the X-ray sensing module when capturing the X-ray image, wherein the control module controls a relative moving speed of the object with respect to the rotation of the X-ray generation module and the X-ray sensing module on the basis of the size information.

According to the present disclosure, the medical X-ray imaging apparatus having the X-ray imaging mechanism optimized according to the size of the object and thus capable of minimizing the imaging time and the amount of radiation exposure is provided.

BRIEF DESCRIPTION OF THE DRAWINGS

The above and other objectives, features, and other advantages of the present disclosure will be more clearly understood from the following detailed description when taken in conjunction with the accompanying drawings, in which.

DETAILED DESCRIPTION OF THE INVENTION

Figure 1:
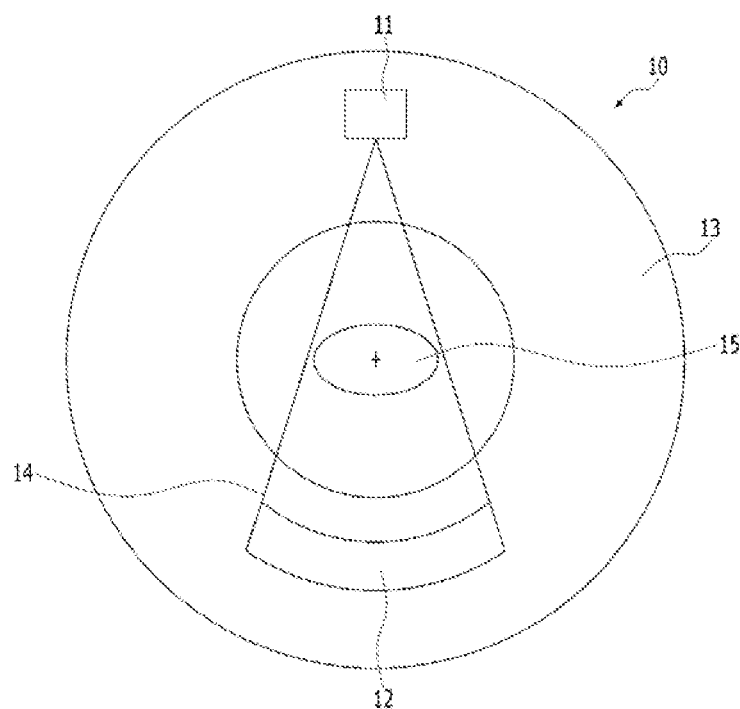
FIG. 1 is a view illustrating an X-ray imaging apparatus in the related art.

The objective, the features, and the advantage that are described above will be understood more clearly from embodiments that are described below with reference to the accompanying drawings.

For illustrative purposes only, embodiments of the present disclosure are described in terms of specific structures and functions. The embodiments of the present disclosure may be implemented in various forms, and the present disclosure should not be interpreted as being limited to the embodiments described in the present specification.

Various modifications may be made to the embodiments of the present disclosure, and thus various embodiments may be created. Among these embodiments, specific embodiments are described in detail in the present specification with reference to the accompanying drawings. However, this detailed description is not intended to limit the embodiments of the present disclosure to specifically disclosed forms. All alterations, equivalents, and substitutes that are included within the technical idea of the present disclosure should be understood as falling within the scope of the present disclosure.

It should be understood that, when a constituent element is referred to as being "coupled to" or "connected to" a different constituent element, this means that the constituent element may be directly coupled to or directly connected to the different constituent element or means that an intervening constituent element may be present therebetween. In contrast, it should be understood that, when a constituent element is referred to as being "directly coupled to" or "directly connected to" a different constituent element, this means that no intervening constituent element is present therebetween. The same may apply to expressions for describing a relationship between constituent elements. For example, expressions such as "between" and "directly between", and expressions such as "adjacent to" and "directly adjacent to" should be construed in the same manner.

The terms used in the present specification are only for describing specific embodiments and are not intended to limit the present disclosure. The indefinite article "a/an" is used to mean one or more, not only one, except as distinctively expressed in context. It should be understood that, in the present specification, the terms "include", "have" and the like are intended to indicate that a feature, a number, a step, an operation, a constituent element, a component, or any combination thereof is present, without precluding the presence or addition of one or more other features, numbers, steps, operations, constituent elements, components or any combination thereof.

Unless otherwise defined, all terms that are used in the present specification, have the same meanings as are normally understood by a person of ordinary skill in the art to which the present disclosure pertains. The term as defined in commonly used dictionaries should be construed as having the same contextual meaning as that in the related art and, unless otherwise explicitly defined in the present specification, should not be construed as having an excessively implied meaning or a purely literal meaning.

An X-ray imaging apparatus according to the present disclosure may acquire size information on an object using an X-ray image of the object. According to the size information on the object, the X-ray imaging apparatus may control a relative moving speed of the object moving toward a direction of a rotation axis of an X-ray generation module and an X-ray sensing module with respect to rotation of a drive mechanism thereof, particularly the X-ray generation module and the X-ray sensing module, when capturing the X-ray image of the object.

More specifically, the X-ray imaging apparatus according to the present disclosure may be a CT imaging apparatus capturing a three-dimensional X-ray image and may capture a two-dimensional X-ray image of the object separately from CT imaging. The two-dimensional X-ray image may be utilized in performing operations, such as object aligning for the CT imaging, imaging area setting, and imaging parameter setting. The X-ray imaging apparatus according to the present disclosure is used for two-dimensional X-ray imaging that is first X-ray imaging. The two-dimensional X-ray imaging is a process in which the object is moved relatively with respect to the X-ray generation module and the X-ray sensing module along the direction of the rotation axis of the X-ray generation module and the X-ray sensing module, with the X-ray generation module and the X-ray sensing module remaining stationary, and in which X-ray image data in one direction is obtained with respect to a length direction of the object. In a control apparatus, the X-ray image data in one direction is reconfigured as the two-dimensional X-ray image with respect to the length direction of the object. Three-dimensional X-ray imaging that is second X-ray imaging is a process in which the object is moved relatively with respect to the X-ray generation module and the X-ray sensing module along the direction of the rotation axis of the X-ray generation module and the X-ray sensing module, with the rotation of the X-ray generation module and the X-ray sensing module being in progress, and in which pieces of X-ray image data in various directions are obtained with respect to the length direction of the object. In the control apparatus, the pieces of X-ray image data in various directions are reconfigured as the three-dimensional X-ray image with respect to the length direction of the object.

In most cases, a cone beam X-ray imaging apparatus is used in the field of dentistry or the like. The cone beam X-ray imaging apparatus detects cone beam X-rays using the X-ray sensing module in the rectangular or square shape and thus acquires X-ray image data having a relatively wide area. Therefore, it is possible that an image of a relatively wide area is captured in a shorter time by X-ray imaging through the use of the cone beam X-rays than by X-ray imaging through the use of fan beam X-rays. However, in a case where the cone beam X-rays are applied to spiral- or helical-type CT imaging, image quality varies widely with a pitch. For this reason, it is very important that a moving speed of an inspection table and/or respective rotation speeds of the X-ray generation module and the X-ray sensing module are suitably adjusted.

For example, in the spiral- or helical-type CT imaging through the use of the cone beam X-rays, when the relative moving speed of the object is low with respect to the rotation of the X-ray generation module and the X-ray sensing module, that is, when a moving speed of the object is relatively low or when the respective rotation speeds of the X-ray generation module and the X-ray sensing module are relatively high, an overlapping X-ray dose between pitches is large and thus an effective data acquisition area (scan field of view (SFOV)) in which an effective image can be obtained after the reconfiguration is performed is increased. For this reason, in a case where the object has a small size, an amount of radiation exposure and the imaging time may be unnecessarily increased. Conversely, when the relative moving speed of the object is high with respect to the rotation of the X-ray generation module and the X-ray sensing module, that is, when the moving speed of the object is relatively high or when the respective rotation speeds of the X-ray generation module and the X-ray sensing module are relatively low, the overlapping X-ray dose between pitches is small, and thus the effective data acquisition area is decreased. For this reason, in a case where the object has a large size, the X-ray image data for the effective image may be insufficient.

The X-ray imaging apparatus according to the present embodiment provides an X-ray imaging mechanism optimized for a size of each object or for a position-based size of the object. This X-ray imaging mechanism is optimized with the following operations: the two-dimensional X-ray image of the object is obtained by the first X-ray imaging; the size information on the object, that is, size information on each object or size information on each of the positions of the object, is obtained with the two-dimensional X-ray image; and the respective rotation speeds of the X-ray generation module and the X-ray sensing module and/or the moving speed of the object for the CT imaging that provides the three-dimensional X-ray image are adjusted according to such size information.

Figure 2:
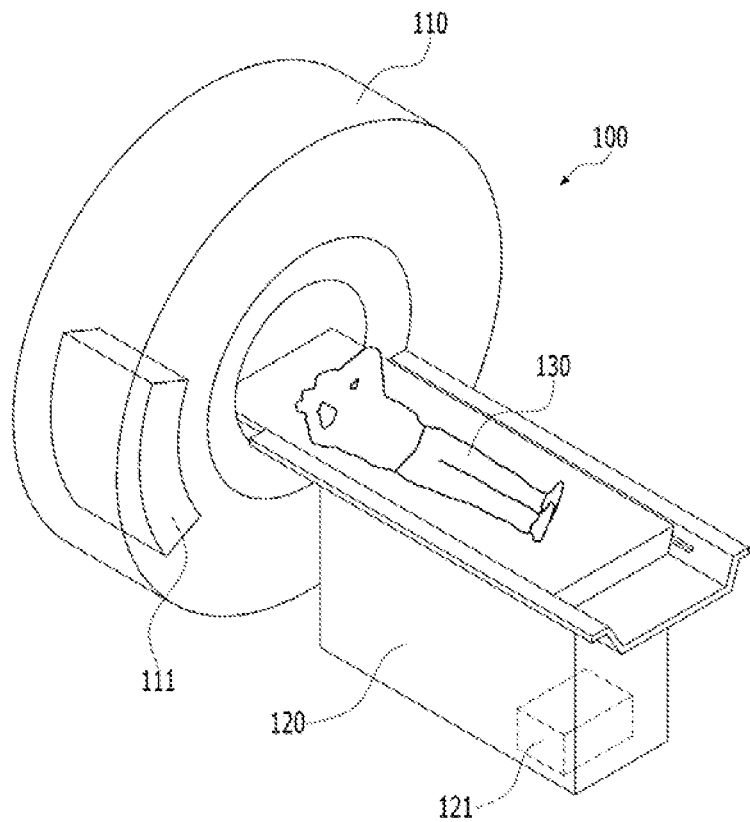
FIG. 2 is a view illustrating an X-ray imaging apparatus according to an embodiment of the prevent disclosure.
Figure 3:
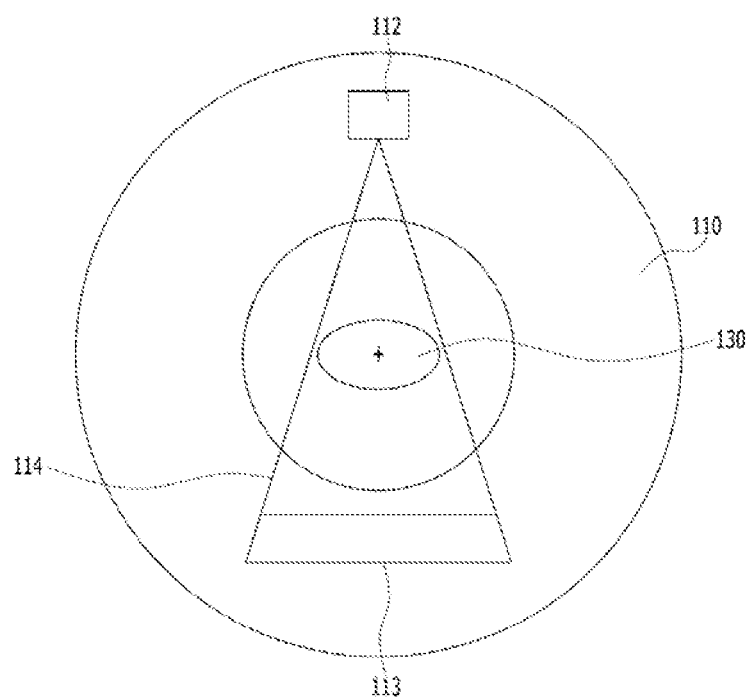
FIG. 3 is a view illustrating an internal structure of the X-ray imaging apparatus according to the embodiment of the present disclosure.
Figure 4:
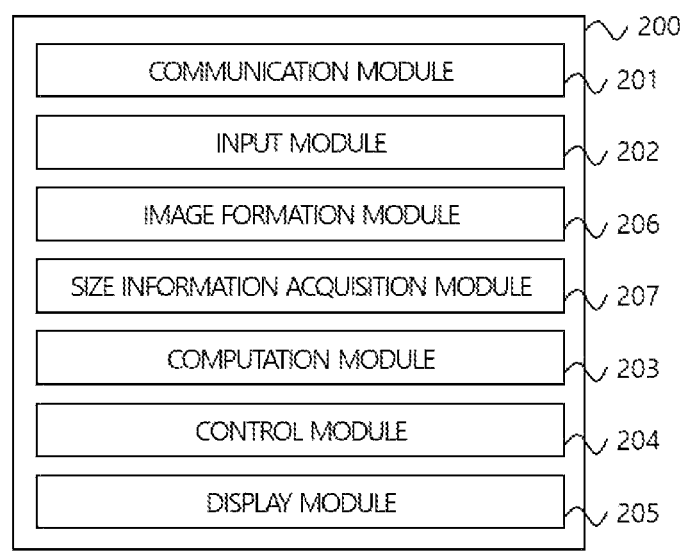
FIG. 4 is a view illustrating a control apparatus according to an embodiment of the present disclosure.

FIG. 2 is a view illustrating an X-ray imaging apparatus according to an embodiment of the prevent disclosure. FIG. 3 is a view illustrating an internal structure of the X-ray imaging apparatus according to the embodiment of the present disclosure. FIG. 4 is a schematic view illustrating a control apparatus according to an embodiment of the present disclosure.

As illustrated in FIGS. 2 to 4, an X-ray imaging apparatus according to the present disclosure may include an imaging body 100 and a control apparatus 200. The imaging body 100 includes a main body 110, an X-ray generation module 112, an X-ray sensing module 113, a first drive device 111, an inspection table 120, and a second drive device 121.

The main body 110 may include a housing in the form of an O-ring or a doughnut that has an opening portion in the center portion thereof. An object 130 may be accommodated into the opening portion in the main body 110. The X-ray generation module 112 and the X-ray sensing module 113 may be provided within the main body 110. The X-ray generation module 112 and the X-ray sensing module 113 may be arranged in such a manner as to face each other with the opening portion in between.

The X-ray generation module 112 may include an X-ray generator and a collimator. The X-ray generator generates X-rays. The collimator adjusts a direction in which the X-rays generated in the X-ray generator are emitted and a magnitude of emission. The X-ray generation module 112 may generate the cone beam X-rays and may emit the generated cone beam X-rays to the object 130. Unlike the fan beam X-rays having a width in a pitch direction, the cone beam X-rays having a large width in a pitch direction may pass through a relatively wide area of the object 130. For this reason, the use of the cone beam X-rays can shorten the imaging time.

The X-ray sensing module 113 includes an X-ray sensor. The X-ray sensor may express a plane with a predetermined area, such as a rectangle or a square.

The X-ray generation module 112 and the X-ray sensing module 113, while rotated about a rotation axis therebetween around the object 130 by the first drive device 111, may emit and detect the X-rays and thus may acquire the pieces of X-ray image data in various directions on the subject 130.

The first drive device 111, provided in a predetermined area of the main body 110, may rotate the X-ray generation module 112 and the X-ray sensing module 113 about the rotation axis therebetween with the object 130 in between and may control respective rotation speeds of the X-ray generation module 112 and the X-ray sensing module 113. The first drive device 111 is not limited to this position and may be positioned at all positions where the X-ray generation module 112 and the X-ray sensing module 113 can be caused to be rotated and where the respective rotation speeds thereof can be controlled.

The first drive device 111 into which a control command is input from the control apparatus 200 may control the respective rotation speeds of the X-ray generation module 112 and the X-ray sensing module 113 according to the control command that is input.

The inspection table 120 may be a bed or a base having a shape similar to that of the bed that can support the object 130.

The inspection table 120 may be moved by the second drive device 121 along the direction of the rotation axis of the X-ray generation module 112 and the X-ray sensing module 113.

The second drive device 121, provided in a predetermined area of the inspection table 120, may move the inspection table 120 along the direction of the rotation axis of the X-ray generation module 112 and the X-ray sensing module 113 through the opening portion in the main body 110 and may control a moving speed of the inspection table 120. The second drive device 121 is not limited to this position and may be positioned at all positions where the inspection table 120 can be caused to be moved and where the moving speed thereof can be controlled.

The second drive device 121 into which a control command is input from the control apparatus 200 may control the moving speed of the inspection table 120 according to the control command that is input.

The control apparatus 200 may include a communication module 201, an input module 202, an image formation module 206, a size information acquisition module 207, a computation module 203, a control module 204, and a display module 205.

The control apparatus 200, provided separately in the shape of a console, may be connected to the main body 110.

The communication module 201 provides communication between the control apparatus 200 and the main body 110, particularly between the control apparatus 200 and each of the X-ray generation module 112, the X-ray sensing module 113, the first drive device 111, and the second drive device 121. The communication module 201 may include a wired or wireless communication device. The X-ray generation module 112, the X-ray sensing module 113, and the first and second drive devices 111 and 121 each may include a wired or wireless communication device for communicating with the communication module 201.

For input, a user operation is applied to the input module 202. Examples of the input module 202 may include a keyboard, a keypad, a touch pad, and the like.

For viewing from the outside, various screens and X-ray images are displayed on the display module 205. Examples of the display module 205 may include an output module, such as a printer, in addition to a display module.

The image formation module 206 may reconfigure the X-ray image using the X-ray image data transferred from the main body 110, particularly the X-ray sensing module 113. The image formation module 206 receives the X-ray image data in one direction on the object 130 from the X-ray sensing module 113 and reconfigures the two-dimensional X-ray image of the object 120. Furthermore, the image formation module 206 receives the pieces of X-ray image data in various directions on the object 130 from the X-ray sensing module 113 and reconfigures the three-dimensional X-ray image of the object 130. The image formation module 206 may include a predetermined algorithm for reconfiguring the two-dimensional and three-dimensional X-ray images.

The size information acquisition module 207 may acquire the size information on each object 130 or the size information on each of the positions of the object 130 on the basis of the two-dimensional X-ray image. When capturing the three-dimensional X-ray image, the computation module 203 may compute the relative moving speed of the object 130 with respect to rotation of the X-ray generation module 112 and the X-ray sensing module 113 according to the size information on each object 130 or the size information on each of the positions of the object 130 that is obtained by the size information acquisition module 207.

The control module 204 controls the X-ray generation module 112, the X-ray sensing module 113, and the first and second drive devices 111 and 121 and thus captures the two-dimensional X-ray image and the three-dimensional X-ray image of the object 130. By controlling the first drive device 111, the control module 204 may keep the X-ray generation module 112 and the X-ray sensing module 113 stationary. In this state, the control module 204 may move the inspection table 120 along the direction of the rotation axis of the X-ray generation module 112 and the X-ray sensing module 113. While the inspection table 120 is moved, the control module 204 may capture the two-dimensional X-ray image in one direction with respect to the object 130 by controlling the X-ray generation module 112 and the X-ray sensing module 113. In addition, by controlling the first and second drive devices 111 and 121, the control module 204 may rotate the X-ray generation module 112 and the X-ray sensing module 113. At the same time, the control module 204 may move the inspection table 120 along the direction of the rotation axis of the X-ray generation module 112 and the X-ray sensing module 113. While the inspection table 120 is moved, by controlling the X-ray generation module 112 and the X-ray sensing module 113, the control module 204 may capture pieces of three-dimensional X-ray image in various directions with respect to the object 130.

The control module 204 may control the first drive device 111 in such a manner that the inspection table 120 is moved at a predetermined moving speed when capturing the two-dimensional X-ray image. The control module 204 may control the first and second drive devices 111 and 121 in such a manner that the X-ray generation module 112 and the X-ray sensing module 113 and the inspection table 120 are rotated and moved, respectively, at the relative moving speed of the object 130 with respect to the rotation of the X-ray generation module 112 and the X-ray sensing module 113 when capturing the three-dimensional X-ray image. The relative moving speed of the object 130 here is computed in the computation module 203.

For reference, the image formation module 206, the size information acquisition module 207, the computation module 203, and the control module 204 may be realized in hardware as at least one of an Application Specific Integrated Circuit (ASIC), a Digital Signal Processor (DSP), a Digital Signal Processing Device (PSPD), a Programmable Logic Device (PLD), a Field-Programmable Gate Array (FPGA), a processor, a control module, a micro-control module, and a microprocessor. Embodiments of the present disclosure that include a procedure, a step, or a function may be realized as a firmware/software module executable on a hardware platform. The firmware/software module causes at least one function or operation to be performed. A software code may be realized by a software application written in a suitable program language. In this case, the software code may be stored in the control module 204 and may be executed.

In addition, the control apparatus 200 may include a storage module in which various pieces of information are stored. The storage module may be one of storage mediums, such as a flash memory, a hard disk, a multimedia card (MMC), a card-type memory (for example, a secure digital (SD) card, an XD(eXtream Digital) card, or the like), a Random Access Memory (RAM), a Static Random Access Memory (SRAM), a Read-Only Memory (ROM), an Electrically Erasable Programmable Read-Only Memory (EEPROM), a Programmable Read-Only Memory (PROM), a magnetic memory, a magnetic disk, and an optical disk.

Figure 5:
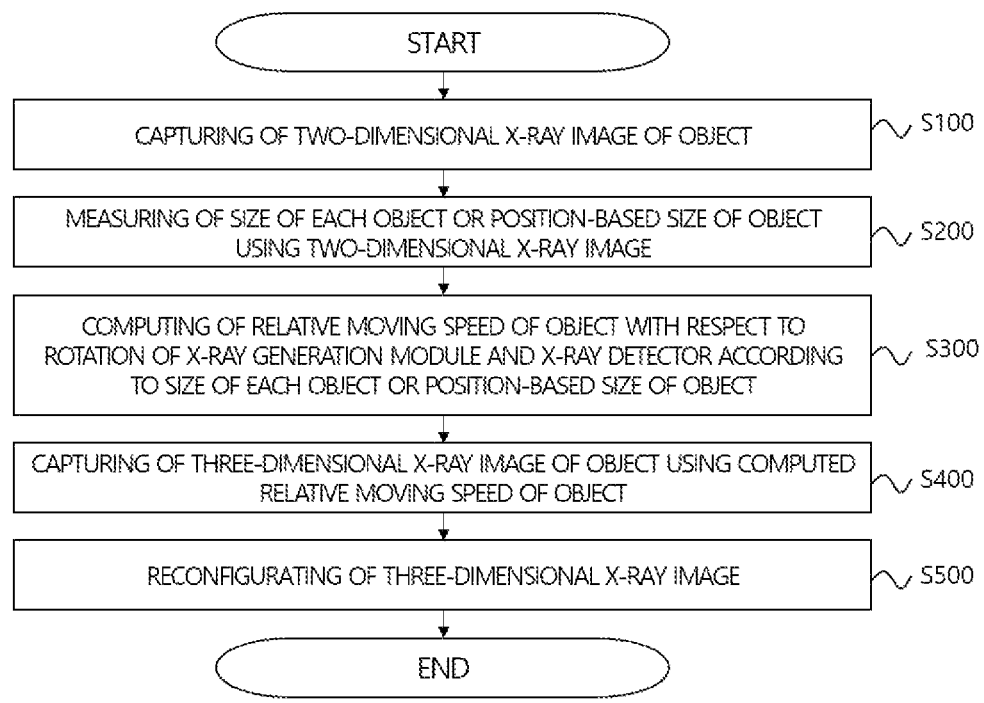
FIG. 5 is a flowchart illustrating an X-ray imaging method that uses the X-ray imaging apparatus according to the present invention.

FIG. 5 is a flowchart illustrating an X-ray imaging method that uses the X-ray imaging apparatus according to the present invention.

As illustrated in FIG. 5, the two-dimensional X-ray image of the object 130 may be captured before capturing the three-dimensional X-ray image (S100). When capturing the two-dimensional X-ray image, the X-ray generation module 112 and the X-ray sensing module 113 of the main body 110 are kept stationary, and only the inspection table 120 is relatively moved with respect to the X-ray generation module 112 and the X-ray sensing module 113 along the direction of the rotation axis of the X-ray generation module 112 and the X-ray sensing module 113. Through this process, the two-dimensional X-ray image of the object 130 is acquired.

To this end, when for input, a user operation for the two-dimensional X-ray imaging is applied to the input module 202, the control module 204 controls the X-ray generation module 112 and the X-ray sensing module 113, and the second drive device 121 in a prestored two-dimensional X-ray imaging mode and thus obtains the X-ray image data in one direction with respect to the object 130. The obtained X-ray image data in one direction is transferred to the image formation module 206, is reconfigured as the two-dimensional X-ray image, and thus is displayed on the display module.

Subsequently, the size of each object 130 or the position-based size of the object 130 may be measured with the two-dimensional X-ray image (S200).

To this end, the size information acquisition module 207 measures the size of each object 130 or the position-based size of the object 130 using the two-dimensional X-ray image. The size here means a length in the leftward-rightward direction of the object 130 that is perpendicular to the rotation axis of the X-ray generation module 112 and the X-ray sensing module 113. A width direction means a direction perpendicular to an X-ray emission direction for the two-dimensional X-ray imaging. When it is assumed that a patient who is the object 130 lies on the inspection table 120, the two-dimensional X-ray image may be a posterior-anterior (PA) image that is a transmission image in the forward-backward direction of the patient or may be a lateral (LAT) image that is a transmission image in the leftward-rightward direction. In the case of the PA image, a length in the width direction of each object 130 or a position-based length in the width direction of the object 130 is a length in the leftward-rightward direction of the patient. In the case of the LAT image, a length in the width direction of each object 130 or a position-based length in the width direction of the object 130 is a length in the forward-backward direction of the patient.

The size information acquisition module 207 may measure the size of each object 130 or the position-based size of the object 130 manually or automatically. In the case of the manual measurement, the size information acquisition module 207 may display the two-dimensional X-ray image on the display module, and a user may measure a length of a line drawn along the width direction of the object 130 using a mouse or like that is the input module 202. That is, on the basis of the two-dimensional X-ray image displayed on the display module, a length in the width direction of the object 130 may be computed by applying the user operation to the input module 202 for inputting.

In the case of the automatic measurement, the size information acquisition module 207 may be equipped with an edge detection algorithm and may detect left and right edge portions of the object 130 using a contrast difference within the two-dimensional X-ray image after executing the edge detection algorithm. Thus, the size information acquisition module 207 may compute the length in the width direction of the object 130.

Subsequently, the computation module 203 may compute the relative moving speed of the object 130 with respect to the rotation of the X-ray generation module 112 and the X-ray sensing module 113 according to the size of each object 130 or the position-based size of the object 130 (S300).

A pitch between X-rays is determined by the relative moving speed of the object 130 with respect to the rotation of the X-ray generation module 112 and the X-ray sensing module 113, and a size of the effective data acquisition area is determined by the pitch.

Figure 6:
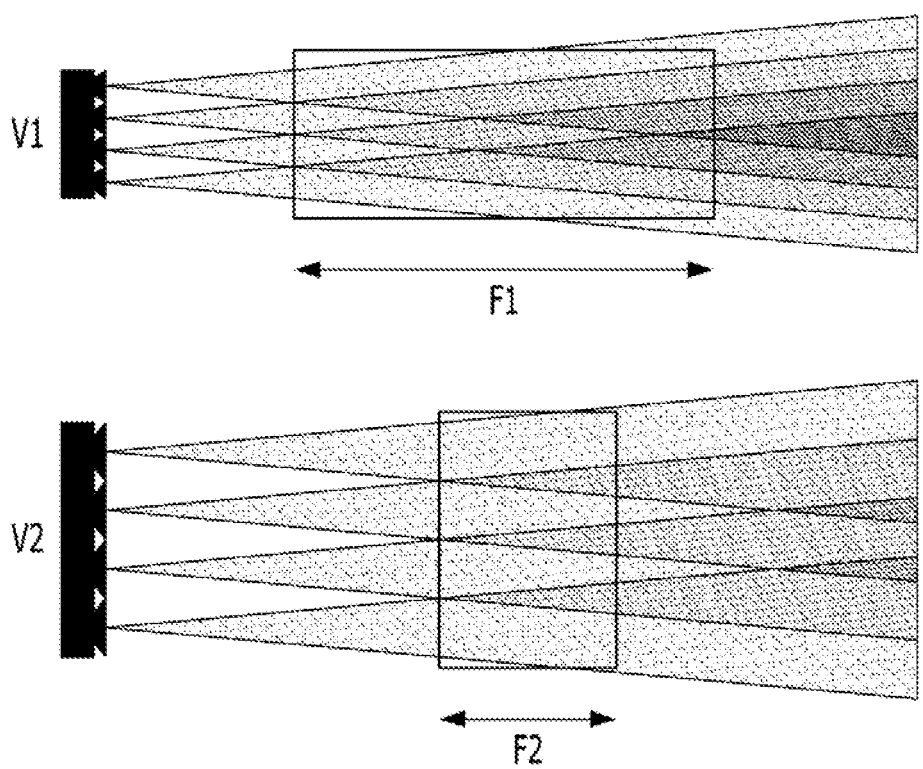
FIG. 6 is a view illustrating a comparison between pitches for objects having different lengths in a width direction and a comparison between effective data acquisition areas.
Figure 7:
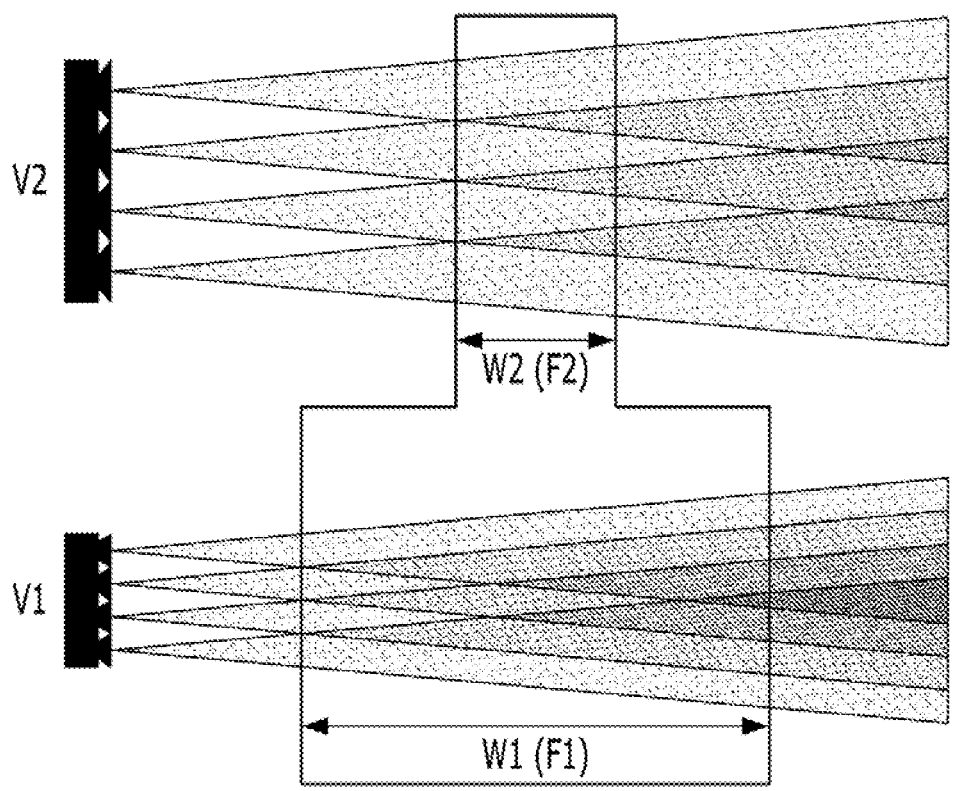
FIG. 7 is a view illustrating a comparison between position-based pitches for an object having different position-based lengths in the width direction and a comparison between effective data acquisition areas.

FIG. 6 is a view illustrating a comparison between pitches for the objects having different lengths in the width direction and a comparison between effective data acquisition areas. FIG. 7 is a view illustrating a comparison between position-based pitches for the object having different position-based lengths in the width direction and a comparison between effective data acquisition areas.

As illustrated in FIG. 6, relative moving speeds of the objects 130 in accordance with sizes of the objects 130, that is, lengths in the width direction of the objects 130 perpendicular to the rotation axis may be compared to find a difference therebetween.

When it is assumed that the respective rotation speeds of the X-ray generation module 112 and the X-ray detection 113 are constant for the purpose of convenience, in a case where a length in the width direction of a first object 130 is greater than a length in the width direction of a second object 130, a relative moving speed V1 of the first object 130 may be smaller than a relative moving speed V2 of the second object 130. Accordingly, the pitch between X-rays may be decreased. As a result, a width F1 of an effective data acquisition area of the first object 130 may be greater than a width F2 of an effective data acquisition area of the second object 130. In this case, it is desirable that the length in the width direction of the object 130 may have a maximum value among lengths in the width direction of the object 130 perpendicular to the rotation axis.

As illustrated in FIG. 7, relative moving speeds of the objects 130 in accordance with position-based sizes of the objects 130, that is, position-based lengths in the width direction of the objects 130 may be compared to find a difference therebetween.

When a length W1 in the width direction at a first position within a first section of the first object 130 is greater than a length W2 in the width direction at a second position within a second section, a relative moving speed V1 of the object 230 in the first section may be lower than a relative moving speed V2 of the inspection table 120 in the second section. Accordingly, a width F1 of the effective data acquisition area in the first section may be greater than a width F2 of the effective data acquisition area in the second section. In this case, it is desirable that the position-based length in the width direction of the object 130 may have a maximum value within a section predetermined on the basis of a position of the object 130.

As illustrated in FIGS. 6 and 7, the size of each object 130 or the position-based size of the object 130 is great, the relative moving speed of the object 130 with respect to the rotation of the X-ray generation module 112 and the X-ray sensing module 113 may be decreased. Furthermore, in a case where the size of the object 130 is small, the relative moving speed of the object 130 with respect to the rotation of the X-ray generation module 112 and the X-ray sensing module 113 may be increased.

As described above, the relative moving speed of the object 130 is adjusted according to the size of each object 130 or the position-based size of the object 130. Thus, an unnecessary dose of radiation to which the object 130 is exposed can be minimized, and an unnecessary amount of data can be minimized. Accordingly, an amount of data and an amount of computation can be minimized. In addition, the entire imaging time can be decreased because the imaging time is optimized for the size of each object 130 or the position-based size of the object 130.

With respect back to FIG. 5, the control module 204 may capture the three-dimensional X-ray image by controlling the first and second drive devices 111 and 121 according to the relative moving speed of the object 130 with respect to the rotation of the X-ray generation module 112 and the X-ray sensing module 113 (S400). The relative moving speed is computed in the computation module 203.

For the relative moving speed of the object 130 with respect to the rotation of the X-ray generation module 112 and the X-ray sensing module 113, the control module 204 may adjust selectively or at the same time the respective rotation speeds of the X-ray generation module 112 and the X-ray sensing module 113 that are rotated by the first drive device 111 and the moving speed of the inspection table 120 that is moved by the second drive device 121.

That is, by controlling the first and second drive devices 111 and 121, the control module 204 may adjust the respective rotation speeds of the X-ray generation module 112 and the X-ray sensing module 113 or the straight-line-moving speed of the inspection table 120, or both on the basis of the object 130 or the position of the object 130. In this case, the respective rotation speeds of the X-ray generation module 112 and the X-ray sensing module 113 are in proportional to the size of the object 130 or the position-based size of the object 130, and the moving speed of the inspection table 120 is in inverse proportion to the size of the object 130 or the position-based size of the object 130.

Subsequently, the image formation module 206 reconfigures the three-dimensional X-ray image using the pieces of X-ray image data in various directions with respect to the object 130 (S500). The pieces of X-ray image data are obtained by capturing the three-dimensional X-ray image. The result of the reconfiguration may be displayed on the display module by applying the user operation to the input module 202.

The inspection table 120 is described above as being separately provided, and the second drive device 121 is described above as adjusting the moving speed of the inspection table 120. However, for reference, it is also possible that the X-ray generation module 112 and the X-ray sensing module 113 can be moved in the direction of the rotation axis whenever necessary in a state where the inspection table 120 remains stationary. Furthermore, it is also possible that the X-ray generation module 112 and the X-ray sensing module 113 can be moved in the direction of the rotation axis while the object 130 is in the upright position without the inspection table 120 being separately provided. Therefore, in a broad sense, the second drive device 121 employs a mechanical configuration in which the object 130 can be moved relatively in the direction of the rotation axis with respect to the X-ray generation module 112 and the X-ray sensing module 113.

As described above, the X-ray imaging apparatus and the X-ray imaging method according to the present disclosure has the following advantage. The drive mechanism for the three-dimensional X-ray imaging can be optimized for the size of the object 130 or the position-based size of the object 130, using the two-dimensional X-ray image that results from the two-dimensional X-ray imaging. Accordingly, the three-dimensional X-ray image can be captured. Thus, the imaging time, the amount of radiation exposure, the image processing time, and the like can be shortened.

Although the specific embodiment of the present disclosure has been described for illustrative purposes, those skilled in the art will appreciate that various modifications, additions and substitutions are possible, without departing from the scope and spirit of the disclosure as disclosed in the accompanying claims.

What is claimed is:

1. An X-ray imaging apparatus comprising:
an imaging body including an X-ray generation device and an X-ray sensing device, wherein the X-ray generating device and the X-ray sensing device are disposed to face each other, and configured to rotate about a rotation axis and acquire X-ray image data of an object including multiple sections;
an inspection table configured to move the object along a direction of the rotation axis between the X-ray generation device and the X-ray sensing device; and
a control circuit configured to:
capture a two-dimensional X-ray image of the object by controlling the imaging body;
acquire size information of the object based on the captured two-dimensional X-ray image of the object by measuring a length of each section of the object, wherein the length of each section is in a direction perpendicular to the rotation axis;
compute a moving speed of each section of the object with respect to rotation of the X-ray generation device and the X-ray sensing device based on the size information; and capture a three-dimensional X-ray image by rotating the X-ray generation device and the X-ray sensing device and moving the inspection table with the object along a direction of the rotation axis based on the computed moving speed, wherein the moving speed of the inspection table is equal to the computed moving speed of each section of the object,
wherein the control circuit controls the moving speed of the inspection table with respect to a rotation speed of the X-ray generation device and the X-ray sensing device based on the computed moving speed of each section of the object while rotating the X-ray generation device and the X-ray sensing device and moving the inspection table for capturing the three-dimensional X-ray image.

2. The X-ray imaging apparatus of claim 1, wherein the imaging body further comprises a first drive device configured to rotate the X-ray generation device and the X-ray sensing device about the rotation axis, and
the control circuit controls the moving speed of the inspection table with respect to the rotation speed of the X-ray generation device and the X-ray sensing device by controlling the first drive device.

3. The X-ray imaging apparatus of claim 1, wherein the imaging body further comprises a second drive device configured to relatively move the inspection table with the object along the direction of the rotation axis with respect to the X-ray generation device and the X-ray sensing device, and
the control circuit controls the moving speed of the inspection table with respect to the rotation speed of the X-ray generation device and the X-ray sensing device by controlling the second drive device.

4. The X-ray imaging apparatus of claim 1, wherein the control circuit further comprises:
a display configured to display the two-dimensional X-ray image; and
an input device configured to receive inputs form a user to perform a predetermined operation, and
the control circuit acquires the size information according to the predetermined operation performed by the inputs entered through the input device, based on the two-dimensional X-ray image displayed on the display.

5. The X-ray imaging apparatus of claim 1, wherein the control circuit measure the length of each section of the object, wherein the length of each section is in a direction perpendicular to the rotation axis, by detecting an edge of the two-dimensional X-ray image using a predetermined edge detection algorithm.

6. The X-ray imaging apparatus of claim 1, the control circuit adjusts a pitch for controlling the moving speed of the inspection table with respect to the rotation of the X-ray generation device and the X-ray sensing device, wherein the pitch is a movement distance of the inspection table with respect to the rotation of the X-ray generating device and the X-ray sensing device.

7. The X-ray imaging apparatus of claim 2, wherein the rotation speed of the X-ray generation device and the X-ray sensing device are in proportion to the length of each section of the object, wherein the length of each section is in a direction perpendicular to the rotation axis.

* * * * *